United States Patent [19]

Inoue et al.

[11] 4,393,219

[45] Jul. 12, 1983

[54] SALT OF CHLORHEXIDINE

[75] Inventors: Koji Inoue, Osaka; Nobukatsu Sato, Nara; Takashi Tamura, Takatsuki, all of Japan

[73] Assignee: Maruishi Pharmaceutical Co., Ltd., Japan

[21] Appl. No.: 301,892

[22] Filed: Sep. 11, 1981

[30] Foreign Application Priority Data

Mar. 30, 1981 [JP] Japan .................................. 56-47043

[51] Int. Cl.$^3$ ............................................ C07D 207/28
[52] U.S. Cl. ..................................... 548/534; 424/274
[58] Field of Search ................... 260/326.45; 564/235; 548/534

[56] References Cited

U.S. PATENT DOCUMENTS 3,183,230 5/1965 Shapiro et al. ...................... 564/235
3,272,863 9/1966 Culter et al. ........................ 564/235
4,059,624 11/1977 Harrison ............................. 564/235

FOREIGN PATENT DOCUMENTS 1344880 1/1974 United Kingdom .

Primary Examiner—Richard Raymond
Attorney, Agent, or Firm—Wenderoth, Lind & Ponack

[57] ABSTRACT

There is provided the novel salt: chlorhexidine di-2-pyrrolidone-5-carboxylate which has potent antibiotic activity and is easily crystallizable.

1 Claim, 2 Drawing Figures

SALT OF CHLORHEXIDINE

BACKGROUND AND PRIOR ART

This invention relates to a novel and pharmaceutically useful salt of chlorhexidine; more particularly, it relates to chlorhexidine di-2-pyrrolidone-5-carboxylate represented by the following chemical formula:

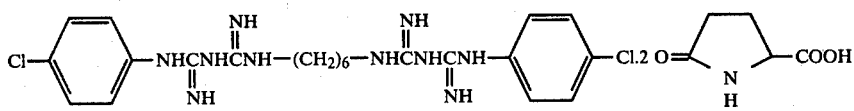 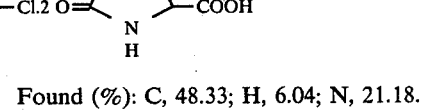

Chlorhexidine is an antiseptic and disinfectant, and is known by such name in The Japanese and British Pharmacopeias, in the form of its hydrochloride.

Of the known salts of chlorhexidine, the dihydrochloride, as well as the disulfate and diacetate, are sparingly soluble in water (cf. 1 g per 10,000 ml) and alcohols such as methanol and ethanol. Consequently, the digluconate is sometimes employed for pharmaceutical preparations because of its superior solubility in water and alcohols. However, it is hard to form crystals of the digluconate, even when the water solution thereof is concentrated to dryness.

An object of this invention is to provide a novel salt of chlorhexidine which is easily soluble in water and alcohols and is easily crystallizable at room temperature, and moreover, which has more potent antibiotic activity than the digluconate.

2-Pyrrolidone-5-carboxylic acid, namely L-pyroglutamic acid, is a known compound which has been used as a chemical reagent, for example, for the resolution of racemic amines (cf. The Merck Index, Ninth Edition, Item No. 7787).

BRIEF DESCRIPTION OF THE INVENTION

The present invention provides a novel salt of chlorhexidine, free from the drawbacks of the prior art, namely, chlorhexidine di-2-pyrrolidone-5-carboxylate.

DETAILED DESCRIPTION OF THE INVENTION

Figure 1:
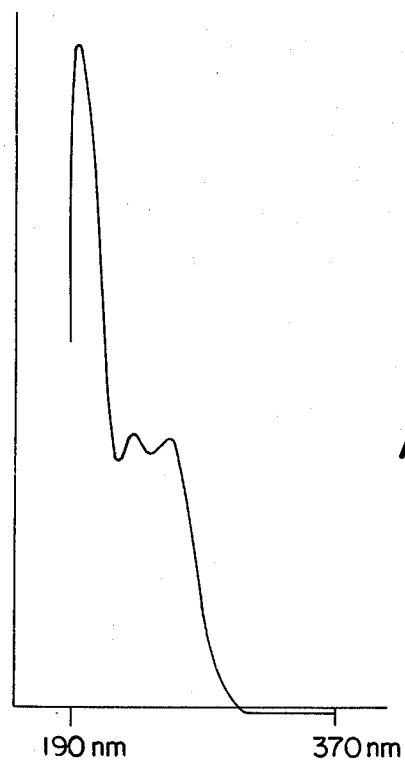
FIG. 1 shows the ultraviolet absorption spectrum of the salt of this invention in 0.001% water solution.
Figure 2:
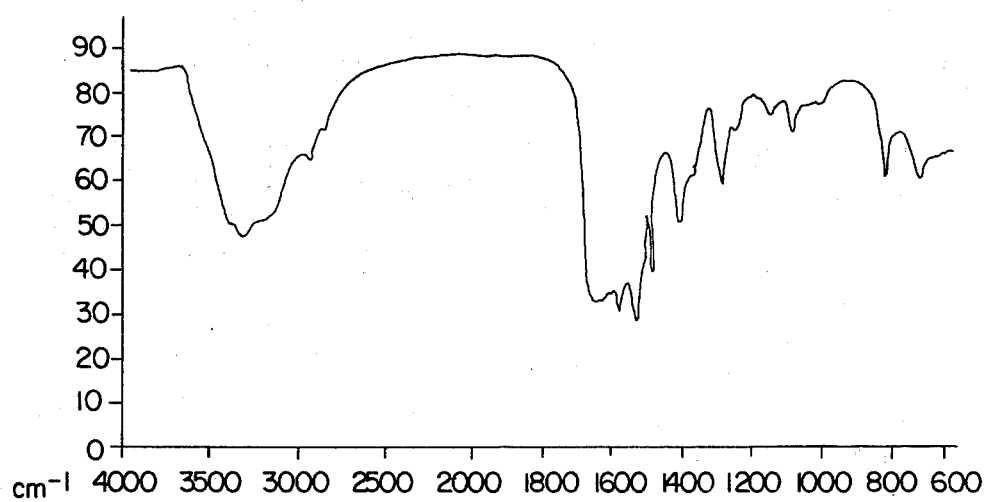
FIG. 2 shows the infrared absorption spectrum of the salt of this invention.

The salt of this invention can be prepared by ordinary processes in the art for making salts.

EXAMPLE

Two moles of 2-pyrrolidone-5-carboxylic acid were dissolved in 50 times their weight of water, into which chlorhexidine was gradually added under stirring. Then the excess of chlorhexidine began to precipitate at the time of just over the equivalent point. The precipitates were removed by filtration and the filtrate was distilled in vacuo to obtain oily materials, which instantly gave a quantitative amount of needle crystals of chlorhexidine di-2-pyrrolidone-5-carboxylate.

Analysis-Calculated for $C_{32}H_{44}Cl_2N_{12}O_6 \cdot 2H_2O$ (mol. wt.: 799.71) Calcd. (%): C, 48.05; H, 6.04; N, 21.02.

Found (%): C, 48.33; H, 6.04; N, 21.18.

The compound is odorless and in the form of white crystals or powder which melts at 152°–154° C. and is soluble in water and alcohols and insoluble in acetone, chloroform and ether.

The ultraviolet and infrared absorption spectra of this compound will be shown in attached Figures.

Antibiotic activities of the compound of this invention will be indicated by following experimental data:

(1) Strains employed:
  *Acinetobacter anitratus* RIMD 0102002
  *Flavobacterium menigosepticum* RIMD 0614002
  *Proteus vulgaris* IFO 3045
  *Pseudomonas aeruginosa* IID 1117
  *Serratia marcescens* IFO 12648

All of these strains are commonly employed in microbiology.

(2) Method:

The experiment was conducted according to the guide method which has been once revised and re-published by Japan Chemotherapy Association by using trypticase soy broth (BBL) as an incubation medium and heart infusion agar as a medium for determining susceptibility.

(3) Minimum inhibitory concentration (μg/ml):

TABLE

| Strain | Chlorhexidine digluconate | Salt of this invention | Pyrrolidone-carboxylic acid |
|---|---|---|---|
| A. anitratus | 62.5 | 31.3 | 4,000 |
| F. menigosepticum | 125 | 31.3 | 4,000 |
| P. vulgaris | 250 | 125 | 4,000 |
| Ps. aeruginosa | 31.3 | 15.6 | 4,000 |
| S. marcescens | 125 | 125 | 4,000 |

From the above Table, it has been determined that the salt of this invention possesses more potent antibiotic activity than the known chlorhexidine digluconate.

The $LD_{50}$ value of this salt is determined to be about 2.0 g/kg of body-weight in mice.

We claim:
1. Chlorhexidine-di-2-pyrrolidone-5-carboxylate.

* * * * *